United States Patent
Pikkula et al.

(10) Patent No.: US 10,765,650 B2
(45) Date of Patent: *Sep. 8, 2020

(54) ARTIFICIAL SALIVA

(71) Applicant: Forward Science Technologies, LLC, Stafford, TX (US)

(72) Inventors: Brian Pikkula, Sugar Land, TX (US); Robert J. Whitman, West University Place, TX (US)

(73) Assignee: Forward Science Technologies, LLC, Stafford, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/179,846

(22) Filed: Nov. 2, 2018

(65) Prior Publication Data

US 2019/0070135 A1 Mar. 7, 2019

Related U.S. Application Data

(63) Continuation-in-part of application No. 15/424,100, filed on Feb. 3, 2017, now Pat. No. 10,143,635.

(60) Provisional application No. 62/290,772, filed on Feb. 3, 2016.

(51) Int. Cl.

| | |
|---|---|
| A61K 31/167 | (2006.01) |
| A61P 1/02 | (2006.01) |
| A61Q 11/00 | (2006.01) |
| A61K 31/245 | (2006.01) |
| A61K 47/02 | (2006.01) |
| A61K 45/06 | (2006.01) |
| A61K 9/08 | (2006.01) |
| A61K 9/00 | (2006.01) |
| A61K 8/24 | (2006.01) |
| A61K 8/42 | (2006.01) |
| A61K 8/44 | (2006.01) |
| A61K 8/19 | (2006.01) |
| A61K 33/42 | (2006.01) |
| A61K 33/06 | (2006.01) |
| A61K 33/00 | (2006.01) |

(52) U.S. Cl.
CPC ............. *A61K 31/167* (2013.01); *A61K 8/19* (2013.01); *A61K 8/24* (2013.01); *A61K 8/42* (2013.01); *A61K 8/445* (2013.01); *A61K 9/0053* (2013.01); *A61K 9/08* (2013.01); *A61K 31/245* (2013.01); *A61K 33/00* (2013.01); *A61K 33/06* (2013.01); *A61K 33/42* (2013.01); *A61K 45/06* (2013.01); *A61K 47/02* (2013.01); *A61P 1/02* (2018.01); *A61Q 11/00* (2013.01)

(58) Field of Classification Search
None
See application file for complete search history.

(56) References Cited

U.S. PATENT DOCUMENTS

| | | | |
|---|---|---|---|
| 5,547,657 A * | 8/1996 | Singleton | A61K 8/345 424/49 |
| 6,306,372 B1 | 10/2001 | Stier | |
| 10,143,635 B2 | 12/2018 | Pikkula et al. | |
| 2006/0182811 A1 | 8/2006 | Edwards et al. | |
| 2011/0086108 A1 | 4/2011 | Weldon | |
| 2014/0294990 A1 | 10/2014 | O'Connor et al. | |
| 2014/0314827 A1 | 10/2014 | Meiman | |
| 2015/0030694 A1 | 1/2015 | Kobus | |
| 2016/0175356 A1* | 6/2016 | Weldon | A61K 9/006 424/602 |
| 2017/0216169 A1 | 8/2017 | Pikkula et al. | |
| 2019/0070080 A1 | 3/2019 | Pikkula et al. | |
| 2019/0070135 A1 | 3/2019 | Pikkula et al. | |

OTHER PUBLICATIONS

Facts and Comparisons® eAnswers—website, url—online.factsandcomparisons.com/MonoDisp.aspx?monoID=fandc-hcp14030&quick=880285%7c5&search=880285%7c5&isstemmed=True&NDCmapping=-1&fromTop=true#firstMatch, accessed on Jul. 13, 2015, Clinical Drug Information, LLC, 1 pg.

The Moisture Seekers. Sjogren's Syndrome Foundation. Apr. 2012. vol. 30. Issue 4. p. 1-16 (Year: 2012).

NeutraSal. Date Retrieved: Jun. 2019. https://www.neutrasal.de/english/. (Year: 2019).

U.S. Appl. No. 16/179,842, filed Nov. 2, 2018.

* cited by examiner

*Primary Examiner* — Celeste A Roney
(74) *Attorney, Agent, or Firm* — Leydig, Voit & Mayer, Ltd.

(57) ABSTRACT

A composition for mixing with water for use as an oral rinse, comprising monobasic sodium phosphate, dibasic sodium phosphate, sodium chloride, calcium chloride, and an analgesic/anaesthetic such as benzocaine/lidocaine.

9 Claims, No Drawings

ARTIFICIAL SALIVA

CROSS-REFERENCE TO RELATED APPLICATIONS

This application is a continuation-in-part to U.S. patent application Ser. No. 15/424,100, filed Feb. 3, 2017 and entitled "Artificial Saliva", now allowed, which claims the benefit of U.S. Provisional Application No. 62/290,772, filed Feb. 3, 2016, the entire disclosures of which are hereby incorporated herein by reference.

BACKGROUND OF THE DISCLOSURE

There are many artificial saliva products intended for human consumption in treating various ails of the human oral cavity. However, such salivary preparations are far from fully satisfactory.

DETAILED DESCRIPTION

It is to be understood that the following disclosure provides many different embodiments, or examples, for implementing different features of various embodiments. Specific examples of components and arrangements are described below to simplify the present disclosure. These are, of course, merely examples and are not intended to be limiting.

The present disclosure introduces an artificial saliva that is provided in disposable packets. The artificial saliva is comprised of powdered ingredients that, when combined with a predetermined amount (e.g., about 30 mL or about 1 oz., or about 3 mL or about 0.1 oz.) of water, produces a supersaturated calcium phosphate solution. The artificial saliva may be packaged in single-use packets. The artificial saliva may be provided non-sterile, and perhaps not intended to be sterilized before use.

The artificial saliva may be administered several times per day. Thus, the artificial saliva may primarily be used at home, office, or other non-clinical settings. However, the artificial saliva may also be used in clinical or healthcare facility settings where patients are receiving inpatient services.

The artificial saliva relieves chronic and temporary xerostomia and mucositis. The artificial saliva is a partial substitute for natural saliva, and is effective to moisten, lubricate, and clean the oral cavity, including the mucosa of the mouth, tongue, and throat. Thus, the artificial saliva may facilitate chewing and speaking, and may also relieve bad breath.

The artificial saliva may be used to treat dryness of the mouth or throat (e.g., hyposalivation, xerostomia, mucositis), regardless of the cause, and regardless of whether the condition is temporary or permanent. The artificial saliva relieves dryness of the oral mucosa and/or ameliorates pain.

The artificial saliva may also be used as an adjunct to standard oral care in treating the mucositis that may be caused by radiation or high dose chemotherapy.

The artificial saliva may also be used for the relief of dryness of the oral mucosa when hyposalivation results from surgery, radiotherapy, chemotherapy, infection or dysfunction of the salivary glands, inflammation of the mouth or throat, fever, emotional factors such as fear or anxiety, obstruction of the salivary ducts, Bell's Palsy, and Sjogren's syndrome. The artificial saliva may also be used for dryness of the oral mucosa occurring from using various drugs, such as antihistamines, atropine, or other anticholinergeic agents that suppress salivary secretion.

The artificial saliva may be used as part of an oral hygiene program for patients with dry mouth. The artificial saliva provides intensive hygiene of the oral cavity, and may be used to help relieve bad taste, relieve offensive nasal discharge, and crusting.

Each use may comprise orally rinsing with the artificial saliva for one minute (or some other predetermined time period) and then expectorating, and perhaps repeating. Thus, the artificial saliva is considered a surface-contacting device with a limited duration of contact. The artificial saliva may be used up to a maximum rinse time of 20 minutes per day (e.g., 2 minutes per application×maximum 10 times per day).

The artificial saliva is formulated as a supersaturated solution of calcium and phosphate ions. The artificial saliva is composed of monobasic and dibasic sodium phosphate, optionally sodium bicarbonate, sodium chloride, and calcium chloride, each of which are USP grade (U.S. Pharmacopeial Convention). The artificial saliva may also include silicon dioxide, which is FCC grade (USP Food Chemicals Codex). The artificial saliva can have an in-solution pH range of 6.25-7.5 (e.g., about 6.69), and is soluble in water. If desired, the pH of the solution can be modified so as to achieve a desired pH, such as by adding an effective amount of an acidic component (e.g., an organic acid and/or an inorganic acid), a basic component (e.g., an organic base and/or an inorganic base), a buffering component, or a combination thereof.

The artificial saliva is packaged as a powder in a sealed packet for mixing with water just prior to use. The amount of powder in the sealed packet may be just sufficient for a single use, which may include two rinsing cycles, such as about 351 mg of the powder.

In the powdered form, the individual components and their respective weight percent may be as in Table 1 below.

TABLE 1

| Ingredient | Weight Percent |
| --- | --- |
| Sodium phosphate, monobasic | 2.8 |
| Sodium phosphate, dibasic | 2.8 |
| Sodium bicarbonate | 4.6 |
| Sodium chloride | 72.6 |
| Calcium chloride | 14.2 |

In another embodiment form, the individual components and their respective weight percent may be as in Table 2 below.

TABLE 2

| Ingredient | Weight Percent |
| --- | --- |
| Sodium phosphate, monobasic | 2.7 |
| Sodium phosphate, dibasic | 2.7 |
| Sodium bicarbonate | 4.3 |
| Sodium chloride | 68. |
| Calcium chloride | 18.6 |
| Silicon dioxide | 2.7 |

However, embodiments other than those in Tables 1 and 2 are also within the scope of the present disclosure, including those in Tables 3 and 4 below.

TABLE 3

| Ingredient | Weight Percent |
| --- | --- |
| Sodium phosphate, monobasic | 0.5-5.0 |
| Sodium phosphate, dibasic | 0.5-5.0 |

TABLE 3-continued

| Ingredient | Weight Percent |
| --- | --- |
| Sodium bicarbonate | 1.0-10.0 |
| Sodium chloride | 55.0-87.5 |
| Calcium chloride | 10.0-30.0 |

TABLE 4

| Ingredient | Weight Percent |
| --- | --- |
| Sodium phosphate, monobasic | 0.5-5.0 |
| Sodium phosphate, dibasic | 0.5-5.0 |
| Sodium bicarbonate | 1.0-10.0 |
| Sodium chloride | 55.0-87.5 |
| Calcium chloride | 10.0-30.0 |
| Silicon dioxide | 0.5-5.0 |

Another set of embodiments that are also included within the scope of the present disclosure Also included within the scope of the present disclosure are individual amounts of monobasic sodium phosphate from about 0.1 wt % to about 25.0 wt %, e.g., from about 0.1 wt % to about 20.0 wt %, from about 0.1 wt % to about 15.0 wt %, from about 0.1 wt % to about 10.0 wt %, from about 0.1 wt % to about 8.0 wt %, from about 0.1 wt % to about 7.0 wt %, from about 0.1 wt % to about 6.0 wt %, from about 0.1 wt % to about 5.0 wt %, from about 0.1 wt % to about 4.5 wt %, from about 0.1 wt % to about 4.0 wt %, from about 0.1 wt % to about 3.5 wt %, from about 0.1 wt % to about 3.0 wt %, from about 0.1 wt % to about 2.5 wt %, from about 0.2 wt % to about 25.0 wt %, from about 0.2 wt % to about 20.0 wt %, from about 0.2 wt % to about 15.0 wt %, from about 0.2 wt % to about 10.0 wt %, from about 0.2 wt % to about 8.0 wt %, from about 0.2 wt % to about 7.0 wt %, from about 0.2 wt % to about 6.0 wt %, from about 0.2 wt % to about 5.0 wt %, from about 0.2 wt % to about 4.5 wt %, from about 0.2 wt % to about 4.0 wt %, from about 0.2 wt % to about 3.5 wt %, from about 0.2 wt % to about 3.0 wt %, from about 0.2 wt % to about 2.5 wt %, from about 0.3 wt % to about 25.0 wt %, from about 0.3 wt % to about 20.0 wt %, from about 0.3 wt % to about 15.0 wt %, from about 0.3 wt % to about 10.0 wt %, from about 0.3 wt % to about 8.0 wt %, from about 0.3 wt % to about 7.0 wt %, from about 0.3 wt % to about 6.0 wt %, from about 0.3 wt % to about 5.0 wt %, from about 0.3 wt % to about 4.5 wt %, from about 0.3 wt % to about 4.0 wt %, from about 0.3 wt % to about 3.5 wt %, from about 0.3 wt % to about 3.0 wt %, from about 0.3 wt % to about 2.5 wt %, from about 0.4 wt % to about 25.0 wt %, from about 0.4 wt % to about 20.0 wt %, from about 0.4 wt % to about 15.0 wt %, from about 0.4 wt % to about 10.0 wt %, from about 0.4 wt % to about 8.0 wt %, from about 0.4 wt % to about 7.0 wt %, from about 0.4 wt % to about 6.0 wt %, from about 0.4 wt % to about 5.0 wt %, from about 0.4 wt % to about 4.5 wt %, from about 0.4 wt % to about 4.0 wt %, from about 0.4 wt % to about 3.5 wt %, from about 0.4 wt % to about 3.0 wt %, from about 0.4 wt % to about 2.5 wt %, from about 0.5 wt % to about 25.0 wt %, from about 0.5 wt % to about 20.0 wt %, from about 0.5 wt % to about 15.0 wt %, from about 0.5 wt % to about 10.0 wt %, from about 0.5 wt % to about 8.0 wt %, from about 0.5 wt % to about 7.0 wt %, from about 0.5 wt % to about 6.0 wt %, from about 0.5 wt % to about 5.0 wt %, from about 0.5 wt % to about 4.5 wt %, from about 0.5 wt % to about 4.0 wt %, from about 0.5 wt % to about 3.5 wt %, from about 0.5 wt % to about 3.0 wt %, from about 0.5 wt % to about 2.5 wt %, from about 0.75 wt % to about 25.0 wt %, from about 0.75 wt % to about 20.0 wt %, from about 0.75 wt % to about 15.0 wt %, from about 0.75 wt % to about 10.0 wt %, from about 0.75 wt % to about 8.0 wt %, from about 0.75 wt % to about 7.0 wt %, from about 0.75 wt % to about 6.0 wt %, from about 0.75 wt % to about 5.0 wt %, from about 0.75 wt % to about 4.5 wt %, from about 0.75 wt % to about 4.0 wt %, from about 0.75 wt % to about 3.5 wt %, from about 0.75 wt % to about 3.0 wt %, from about 0.75 wt % to about 2.5 wt %, from about 1.0 wt % to about 25.0 wt %, from about 1.0 wt % to about 20.0 wt %, from about 1.0 wt % to about 15.0 wt %, from about 1.0 wt % to about 10.0 wt %, from about 1.0 wt % to about 8.0 wt %, from about 1.0 wt % to about 7.0 wt %, from about 1.0 wt % to about 6.0 wt %, from about 1.0 wt % to about 5.0 wt %, from about 1.0 wt % to about 4.5 wt %, from about 1.0 wt % to about 4.0 wt %, from about 1.0 wt % to about 3.5 wt %, from about 1.0 wt % to about 3.0 wt %, from about 1.0 wt % to about 2.5 wt %, from about 1.25 wt % to about 25.0 wt %, from about 1.25 wt % to about 20.0 wt %, from about 1.25 wt % to about 15.0 wt %, from about 1.25 wt % to about 10.0 wt %, from about 1.25 wt % to about 8.0 wt %, from about 1.25 wt % to about 7.0 wt %, from about 1.25 wt % to about 6.0 wt %, from about 1.25 wt % to about 5.0 wt %, from about 1.25 wt % to about 4.5 wt %, from about 1.25 wt % to about 4.0 wt %, from about 1.25 wt % to about 3.5 wt %, from about 1.25 wt % to about 3.0 wt %, from about 1.25 wt % to about 2.5 wt %, from about 1.5 wt % to about 25.0 wt %, from about 1.5 wt % to about 20.0 wt %, from about 1.5 wt % to about 15.0 wt %, from about 1.5 wt % to about 10.0 wt %, from about 1.5 wt % to about 8.0 wt %, from about 1.5 wt % to about 7.0 wt %, from about 1.5 wt % to about 6.0 wt %, from about 1.5 wt % to about 5.0 wt %, from about 1.5 wt % to about 4.5 wt %, from about 1.5 wt % to about 4.0 wt %, from about 1.5 wt % to about 3.5 wt %, from about 1.5 wt % to about 3.0 wt %, from about 1.5 wt % to about 2.5 wt %, from about 2.0 wt % to about 25.0 wt %, from about 2.0 wt % to about 20.0 wt %, from about 2.0 wt % to about 15.0 wt %, from about 2.0 wt % to about 10.0 wt %, from about 2.0 wt % to about 8.0 wt %, from about 2.0 wt % to about 7.0 wt %, from about 2.0 wt % to about 6.0 wt %, from about 2.0 wt % to about 5.0 wt %, from about 2.0 wt % to about 4.5 wt %, from about 2.0 wt % to about 4.0 wt %, from about 2.0 wt % to about 3.5 wt %, from about 2.0 wt % to about 3.0 wt %, from about 2.0 wt % to about 2.5 wt %, from about 2.5 wt % to about 25.0 wt %, from about 2.5 wt % to about 20.0 wt %, from about 2.5 wt % to about 15.0 wt %, from about 2.5 wt % to about 10.0 wt %, from about 2.5 wt % to about 8.0 wt %, from about 2.5 wt % to about 7.0 wt %, from about 2.5 wt % to about 6.0 wt %, from about 2.5 wt % to about 5.0 wt %, from about 2.5 wt % to about 4.5 wt %, from about 2.5 wt % to about 4.0 wt %, from about 2.5 wt % to about 3.5 wt %, from about 2.5 wt % to about 3.0 wt %, from about 3.0 wt % to about 25.0 wt %, from about 3.0 wt % to about 20.0 wt %, from about 3.0 wt % to about 15.0 wt %, from about 3.0 wt % to about 10.0 wt %, from about 3.0 wt % to about 8.0 wt %, from about 3.0 wt % to about 7.0 wt %, from about 3.0 wt % to about 6.0 wt %, from about 3.0 wt % to about 5.0 wt %, from about 3.0 wt % to about 4.5 wt %, from about 3.0 wt % to about 4.0 wt %, or from about 3.0 wt % to about 3.5 wt %.

Also included within the scope of the present disclosure are individual amounts of dibasic sodium phosphate from about 0.1 wt % to about 25.0 wt %, e.g., from about 0.1 wt % to about 20.0 wt %, from about 0.1 wt % to about 15.0 wt %, from about 0.1 wt % to about 10.0 wt %, from about 0.1 wt % to about 8.0 wt %, from about 0.1 wt % to about 7.0 wt %, from about 0.1 wt % to about 6.0 wt %, from about 0.1 wt % to about 5.0 wt %, from about 0.1 wt % to about 4.5 wt %, from about 0.1 wt % to about 4.0 wt %, from about 0.1 wt % to about 3.5 wt %, from about 0.1 wt % to about 3.0 wt %, from about 0.1 wt % to about 2.5 wt %, from about 0.2 wt % to about 25.0 wt %, from about 0.2 wt % to about 20.0 wt %, from about 0.2 wt % to about 15.0 wt %, from about 0.2 wt % to about 10.0 wt %, from about 0.2 wt % to about 8.0 wt %, from about 0.2 wt % to about 7.0 wt %, from about 0.2 wt % to about 6.0 wt %, from about 0.2 wt % to about 5.0 wt %, from about 0.2 wt % to about 4.5 wt %, from about 0.2 wt % to about 4.0 wt %, from about 0.2 wt % to about 3.5 wt %, from about 0.2 wt % to about 3.0 wt %, from about 0.2 wt % to about 2.5 wt %, from about 0.3 wt % to about 25.0 wt %, from about 0.3 wt % to about 20.0 wt %, from about 0.3 wt % to about 15.0 wt %, from about 0.3 wt % to about 10.0 wt %, from about 0.3 wt % to about 8.0 wt %, from about 0.3 wt % to about 7.0 wt %, from about 0.3 wt % to about 6.0 wt %, from about 0.3 wt % to about 5.0 wt %, from about 0.3 wt % to about 4.5 wt %, from about 0.3 wt % to about 4.0 wt %, from about 0.3 wt % to about 3.5 wt %, from about 0.3 wt % to about 3.0 wt %, from about 0.3 wt % to about 2.5 wt %, from about 0.4 wt % to about 25.0 wt %, from about 0.4 wt % to about 20.0 wt %, from about 0.4 wt % to about 15.0 wt %, from about 0.4 wt % to about 10.0 wt %, from about 0.4 wt % to about 8.0 wt %, from about 0.4 wt % to about 7.0 wt %, from about 0.4 wt % to about 6.0 wt %, from about 0.4 wt % to about 5.0 wt %, from about 0.4 wt % to about 4.5 wt %, from about 0.4 wt % to about 4.0 wt %, from about 0.4 wt % to about 3.5 wt %, from about 0.4 wt % to about 3.0 wt %, from about 0.4 wt % to about 2.5 wt %, from about 0.5 wt % to about 25.0 wt %, from about 0.5 wt % to about 20.0 wt %, from about 0.5 wt % to about 15.0 wt %, from about 0.5 wt % to about 10.0 wt %, from about 0.5 wt % to about 8.0 wt %, from about 0.5 wt % to about 7.0 wt %, from about 0.5 wt % to about 6.0 wt %, from about 0.5 wt % to about 5.0 wt %, from about 0.5 wt % to about 4.5 wt %, from about 0.5 wt % to about 4.0 wt %, from about 0.5 wt % to about 3.5 wt %, from about 0.5 wt % to about 3.0 wt %, from about 0.5 wt % to about 2.5 wt %, from about 0.75 wt % to about 25.0 wt %, from about 0.75 wt % to about 20.0 wt %, from about 0.75 wt % to about 15.0 wt %, from about 0.75 wt % to about 10.0 wt %, from about 0.75 wt % to about 8.0 wt %, from about 0.75 wt % to about 7.0 wt %, from about 0.75 wt % to about 6.0 wt %, from about 0.75 wt % to about 5.0 wt %, from about 0.75 wt % to about 4.5 wt %, from about 0.75 wt % to about 4.0 wt %, from about 0.75 wt % to about 3.5 wt %, from about 0.75 wt % to about 3.0 wt %, from about 0.75 wt % to about 2.5 wt %, from about 1.0 wt % to about 25.0 wt %, from about 1.0 wt % to about 20.0 wt %, from about 1.0 wt % to about 15.0 wt %, from about 1.0 wt % to about 10.0 wt %, from about 1.0 wt % to about 8.0 wt %, from about 1.0 wt % to about 7.0 wt %, from about 1.0 wt % to about 6.0 wt %, from about 1.0 wt % to about 5.0 wt %, from about 1.0 wt % to about 4.5 wt %, from about 1.0 wt % to about 4.0 wt %, from about 1.0 wt % to about 3.5 wt %, from about 1.0 wt % to about 3.0 wt %, from about 1.0 wt % to about 2.5 wt %, from about 1.25 wt % to about 25.0 wt %, from about 1.25 wt % to about 20.0 wt %, from about 1.25 wt % to about 15.0 wt %, from about 1.25 wt % to about 10.0 wt %, from about 1.25 wt % to about 8.0 wt %, from about 1.25 wt % to about 7.0 wt %, from about 1.25 wt % to about 6.0 wt %, from about 1.25 wt % to about 5.0 wt %, from about 1.25 wt % to about 4.5 wt %, from about 1.25 wt % to about 4.0 wt %, from about 1.25 wt % to about 3.5 wt %, from about 1.25 wt % to about 3.0 wt %, from about 1.25 wt % to about 2.5 wt %, from about 1.5 wt % to about 25.0 wt %, from about 1.5 wt % to about 20.0 wt %, from about 1.5 wt % to about 15.0 wt %, from about 1.5 wt % to about 10.0 wt %, from about 1.5 wt % to about 8.0 wt %, from about 1.5 wt % to about 7.0 wt %, from about 1.5 wt % to about 6.0 wt %, from about 1.5 wt % to about 5.0 wt %, from about 1.5 wt % to about 4.5 wt %, from about 1.5 wt % to about 4.0 wt %, from about 1.5 wt % to about 3.5 wt %, from about 1.5 wt % to about 3.0 wt %, from about 1.5 wt % to about 2.5 wt %, from about 2.0 wt % to about 25.0 wt %, from about 2.0 wt % to about 20.0 wt %, from about 2.0 wt % to about 15.0 wt %, from about 2.0 wt % to about 10.0 wt %, from about 2.0 wt % to about 8.0 wt %, from about 2.0 wt % to about 7.0 wt %, from about 2.0 wt % to about 6.0 wt %, from about 2.0 wt % to about 5.0 wt %, from about 2.0 wt % to about 4.5 wt %, from about 2.0 wt % to about 4.0 wt %, from about 2.0 wt % to about 3.5 wt %, from about 2.0 wt % to about 3.0 wt %, from about 2.0 wt % to about 2.5 wt %, from about 2.5 wt % to about 25.0 wt %, from about 2.5 wt % to about 20.0 wt %, from about 2.5 wt % to about 15.0 wt %, from about 2.5 wt % to about 10.0 wt %, from about 2.5 wt % to about 8.0 wt %, from about 2.5 wt % to about 7.0 wt %, from about 2.5 wt % to about 6.0 wt %, from about 2.5 wt % to about 5.0 wt %, from about 2.5 wt % to about 4.5 wt %, from about 2.5 wt % to about 4.0 wt %, from about 2.5 wt % to about 3.5 wt %, from about 2.5 wt % to about 3.0 wt %, from about 3.0 wt % to about 25.0 wt %, from about 3.0 wt % to about 20.0 wt %, from about 3.0 wt % to about 15.0 wt %, from about 3.0 wt % to about 10.0 wt %, from about 3.0 wt % to about 8.0 wt %, from about 3.0 wt % to about 7.0 wt %, from about 3.0 wt % to about 6.0 wt %, from about 3.0 wt % to about 5.0 wt %, from about 3.0 wt % to about 4.5 wt %, from about 3.0 wt % to about 4.0 wt %, or from about 3.0 wt % to about 3.5 wt %.

Also included within the scope of the present disclosure are individual amounts of sodium bicarbonate, when present, from about 0.1 wt % to about 25.0 wt %, e.g., from about 0.1 wt % to about 20.0 wt %, from about 0.1 wt % to about 15.0 wt %, from about 0.1 wt % to about 10.0 wt %, from about 0.1 wt % to about 8.0 wt %, from about 0.1 wt % to about 7.0 wt %, from about 0.1 wt % to about 6.0 wt %, from about 0.1 wt % to about 5.0 wt %, from about 0.1 wt % to about 4.5 wt %, from about 0.1 wt % to about 4.0 wt %, from about 0.1 wt % to about 3.5 wt %, from about 0.1 wt % to about 3.0 wt %, from about 0.1 wt % to about 2.5 wt %, from about 0.2 wt % to about 25.0 wt %, from about 0.2 wt % to about 20.0 wt %, from about 0.2 wt % to about 15.0 wt %, from about 0.2 wt % to about 10.0 wt %, from about 0.2 wt % to about 8.0 wt %, from about 0.2 wt % to about 7.0 wt %, from about 0.2 wt % to about 6.0 wt %, from about 0.2 wt % to about 5.0 wt %, from about 0.2 wt % to about 4.5 wt %, from about 0.2 wt % to about 4.0 wt %, from about 0.2 wt % to about 3.5 wt %, from about 0.2 wt % to about 3.0 wt %, from about 0.2 wt % to about 2.5 wt %, from about 0.3 wt % to about 25.0 wt %, from about 0.3 wt % to about 20.0 wt %, from about 0.3 wt % to about 15.0 wt %, from about 0.3 wt % to about 10.0 wt %, from about 0.3 wt % to about 8.0 wt %, from about 0.3 wt % to about 7.0 wt %, from about 0.3 wt % to about 6.0 wt %, from about 0.3 wt % to about 5.0 wt %, from about 0.3 wt % to about 4.5 wt %, from about 0.3 wt % to about 4.0 wt %, from about 0.3 wt % to about 3.5 wt %, from about 0.3 wt % to about 3.0 wt %, from about 0.3 wt % to about 2.5 wt %, from about 0.4 wt % to about 25.0 wt %, from about 0.4 wt % to about 20.0 wt %, from about 0.4 wt % to about 15.0 wt %, from about 0.4 wt % to about 10.0 wt %, from about 0.4 wt % to about 8.0 wt %, from about 0.4 wt % to about 7.0 wt %, from about 0.4 wt % to about 6.0 wt %, from about 0.4 wt % to about 5.0 wt %, from about 0.4 wt % to about 4.5 wt %, from about 0.4 wt % to about 4.0 wt %, from about 0.4 wt % to about 3.5 wt %, from about 0.4 wt % to about 3.0 wt %, from about 0.4 wt % to about 2.5 wt %, from about 0.5 wt % to about 25.0 wt %, from about 0.5 wt % to about 20.0 wt %, from about 0.5 wt % to about 15.0 wt %, from about 0.5 wt % to about 10.0 wt %, from about 0.5 wt % to about 8.0 wt %, from about 0.5 wt % to about 7.0 wt %, from about 0.5 wt % to about 6.0 wt %, from about 0.5 wt % to about 5.0 wt %, from about 0.5 wt % to about 4.5 wt %, from about 0.5 wt % to about 4.0 wt %, from about 0.5 wt % to about 3.5 wt %, from about 0.5 wt % to about 3.0 wt %, from about 0.5 wt % to about 2.5 wt %, from about 0.75 wt % to about 25.0 wt %, from about 0.75 wt % to about 20.0 wt %, from about 0.75 wt % to about 15.0 wt %, from about 0.75 wt % to about 10.0 wt %, from about 0.75 wt % to about 8.0 wt %, from about 0.75 wt % to about 7.0 wt %, from about 0.75 wt % to about 6.0 wt %, from about 0.75 wt % to about 5.0 wt %, from about 0.75 wt % to about 4.5 wt %, from about 0.75 wt % to about 4.0 wt %, from about 0.75 wt % to about 3.5 wt %, from about 0.75 wt % to about 3.0 wt %, from about 0.75 wt % to about 2.5 wt %, from about 1.0 wt % to about 25.0 wt %, from about 1.0 wt % to about 20.0 wt %, from about 1.0 wt % to about 15.0 wt %, from about 1.0 wt % to about 10.0 wt %, from about 1.0 wt % to about 8.0 wt %, from about 1.0 wt % to about 7.0 wt %, from about 1.0 wt % to about 6.0 wt %, from about 1.0 wt % to about 5.0 wt %, from about 1.0 wt % to about 4.5 wt %, from about 1.0 wt % to about 4.0 wt %, from about 1.0 wt % to about 3.5 wt %, from about 1.0 wt % to about 3.0 wt %, from about 1.0 wt % to about 2.5 wt %, from about 1.25 wt % to about 25.0 wt %, from about 1.25 wt % to about 20.0 wt %, from about 1.25 wt % to about 15.0 wt %, from about 1.25 wt % to about 10.0 wt %, from about 1.25 wt % to about 8.0 wt %, from about 1.25 wt % to about 7.0 wt %, from about 1.25 wt % to about 6.0 wt %, from about 1.25 wt % to about 5.0 wt %, from about 1.25 wt % to about 4.5 wt %, from about 1.25 wt % to about 4.0 wt %, from about 1.25 wt % to about 3.5 wt %, from about 1.25 wt % to about 3.0 wt %, from about 1.25 wt % to about 2.5 wt %, from about 1.5 wt % to about 25.0 wt %, from about 1.5 wt % to about 20.0 wt %, from about 1.5 wt % to about 15.0 wt %, from about 1.5 wt % to about 10.0 wt %, from about 1.5 wt % to about 8.0 wt %, from about 1.5 wt % to about 7.0 wt %, from about 1.5 wt % to about 6.0 wt %, from about 1.5 wt % to about 5.0 wt %, from about 1.5 wt % to about 4.5 wt %, from about 1.5 wt % to about 4.0 wt %, from about 1.5 wt % to about 3.5 wt %, from about 1.5 wt % to about 3.0 wt %, from about 1.5 wt % to about 2.5 wt %, from about 2.0 wt % to about 25.0 wt %, from about 2.0 wt % to about 20.0 wt %, from about 2.0 wt % to about 15.0 wt %, from about 2.0 wt % to about 10.0 wt %, from about 2.0 wt % to about 8.0 wt %, from about 2.0 wt % to about 7.0 wt %, from about 2.0 wt % to about 6.0 wt %, from about 2.0 wt % to about 5.0 wt %, from about 2.0 wt % to about 4.5 wt %, from about 2.0 wt % to about 4.0 wt %, from about 2.0 wt % to about 3.5 wt %, from about 2.0 wt % to about 3.0 wt %, from about 2.0 wt % to about 2.5 wt %, from about 2.5 wt % to about 25.0 wt %, from about 2.5 wt % to about 20.0 wt %, from about 2.5 wt % to about 15.0 wt %, from about 2.5 wt % to about 10.0 wt %, from about 2.5 wt % to about 8.0 wt %, from about 2.5 wt % to about 7.0 wt %, from about 2.5 wt % to about 6.0 wt %, from about 2.5 wt % to about 5.0 wt %, from about 2.5 wt % to about 4.5 wt %, from about 2.5 wt % to about 4.0 wt %, from about 2.5 wt % to about 3.5 wt %, from about 2.5 wt % to about 3.0 wt %, from about 3.0 wt % to about 25.0 wt %, from about 3.0 wt % to about 20.0 wt %, from about 3.0 wt % to about 15.0 wt %, from about 3.0 wt % to about 10.0 wt %, from about 3.0 wt % to about 8.0 wt %, from about 3.0 wt % to about 7.0 wt %, from about 3.0 wt % to about 6.0 wt %, from about 3.0 wt % to about 5.0 wt %, from about 3.0 wt % to about 4.5 wt %, from about 3.0 wt % to about 4.0 wt %, or from about 3.0 wt % to about 3.5 wt %. In various embodiments, sodium carbonate can be optional, and may be particularly absent in embodiments where the sodium bicarbonate may detrimentally interact with a therapeutic component and/or may interfere (more than de minimis) with the therapeutic effectiveness of a therapeutic component (e.g., when benzocaine and/or lidocaine are present).

Also included within the scope of the present disclosure are individual amounts of sodium chloride from about 30.0 wt % to about 90.0 wt %, e.g., from about 30.0 wt % to about 87.5 wt %, from about 30.0 wt % to about 85.0 wt %, from about 30.0 wt % to about 82.5 wt %, from about 30.0 wt % to about 80.0 wt %, from about 30.0 wt % to about 77.5 wt %, from about 30.0 wt % to about 75.0 wt %, from about 30.0 wt % to about 72.5 wt %, from about 30.0 wt % to about 70.0 wt %, from about 30.0 wt % to about 67.5 wt %, from about 30.0 wt % to about 65.0 wt %, from about 30.0 wt % to about 62.5 wt %, from about 30.0 wt % to about 60.0 wt %, from about 30.0 wt % to about 57.5 wt %, from about 30.0 wt % to about 55.0 wt %, from about 30.0 wt % to about 52.5 wt %, from about 30.0 wt % to about 50.0 wt %, from about 30.0 wt % to about 47.5 wt %, from about 30.0 wt % to about 45.0 wt %, from about 35.0 wt % to about 90.0 wt %, from about 35.0 wt % to about 87.5 wt %, from about 35.0 wt % to about 85.0 wt %, from about 35.0 wt % to about 82.5 wt %, from about 35.0 wt % to about 80.0 wt %, from about 35.0 wt % to about 77.5 wt %, from about 35.0 wt % to about 75.0 wt %, from about 35.0 wt % to about 72.5 wt %, from about 35.0 wt % to about 70.0 wt %, from about 35.0 wt % to about 67.5 wt %, from about 35.0 wt % to about 65.0 wt %, from about 35.0 wt % to about 62.5 wt %, from about 35.0 wt % to about 60.0 wt %, from about 35.0 wt % to about 57.5 wt %, from about 35.0 wt % to about 55.0 wt %, from about 35.0 wt % to about 52.5 wt %, from about 35.0 wt % to about 50.0 wt %, from about 35.0 wt % to about 47.5 wt %, from about 35.0 wt % to about 45.0 wt %, from about 40.0 wt % to about 90.0 wt %, from about 40.0 wt % to about 87.5 wt %, from about 40.0 wt % to about 85.0 wt %, from about 40.0 wt % to about 82.5 wt %, from about 40.0 wt % to about 80.0 wt %, from about 40.0 wt % to about 77.5 wt %, from about 40.0 wt % to about 75.0 wt %, from about 40.0 wt % to about 72.5 wt %, from about 40.0 wt % to about 70.0 wt %, from about 40.0 wt % to about 67.5 wt %, from about 40.0 wt % to about 65.0 wt %, from about 40.0 wt % to about 62.5 wt %, from about 40.0 wt % to about 60.0 wt %, from about 40.0 wt % to about 57.5 wt %, from about 40.0 wt % to about 55.0 wt %, from about 40.0 wt % to about 52.5 wt %, from about 40.0 wt % to about 50.0 wt %, from about 40.0 wt % to about 47.5 wt %, from about 40.0 wt % to about 45.0 wt %, from about 45.0 wt % to about 90.0 wt %, from about 45.0 wt % to about 87.5 wt %, from about 45.0 wt % to about 85.0 wt %, from about 45.0 wt % to about 82.5 wt %, from about 45.0 wt % to about 80.0 wt %, from about 45.0 wt % to about 77.5 wt %, from about 45.0 wt % to about 75.0 wt %, from about 45.0 wt % to about 72.5 wt %, from about 45.0 wt % to about 70.0 wt %, from about 45.0 wt % to about 67.5 wt %, from about 45.0 wt % to about 65.0 wt %, from about 45.0 wt % to about 62.5 wt %, from about 45.0 wt % to about 60.0 wt %, from about 45.0 wt % to about 57.5 wt %, from about 45.0 wt % to about 55.0 wt %, from about 45.0 wt % to about 52.5 wt %, from about 45.0 wt % to about 50.0 wt %, from about 50.0 wt % to about 90.0 wt %, from about 50.0 wt % to about 87.5 wt %, from about 50.0 wt % to about 85.0 wt %, from about 50.0 wt % to about 82.5 wt %, from about 50.0 wt % to about 80.0 wt %, from about 50.0 wt % to about 77.5 wt %, from about 50.0 wt % to about 75.0 wt %, from about 50.0 wt % to about 72.5 wt %, from about 50.0 wt % to about 70.0 wt %, from about 50.0 wt % to about 67.5 wt %, from about 50.0 wt % to about 65.0 wt %, from about 50.0 wt % to about 62.5 wt %, from about 50.0 wt % to about 60.0 wt %, from about 50.0 wt % to about 57.5 wt %, from about 50.0 wt % to about 55.0 wt %, from about 55.0 wt % to about 90.0 wt %, from about 55.0 wt % to about 87.5 wt %, from about 55.0 wt % to about 85.0 wt %, from about 55.0 wt % to about 82.5 wt %, from about 55.0 wt % to about 80.0 wt %, from about 55.0 wt % to about 77.5 wt %, from about 55.0 wt % to about 75.0 wt %, from about 55.0 wt % to about 72.5 wt %, from about 55.0 wt % to about 70.0 wt %, from about 55.0 wt % to about 67.5 wt %, from about 55.0 wt % to about 65.0 wt %, from about 55.0 wt % to about 62.5 wt %, from about 55.0 wt % to about 60.0 wt %, from about 60.0 wt % to about 90.0 wt %, from about 60.0 wt % to about 87.5 wt %, from about 60.0 wt % to about 85.0 wt %, from about 60.0 wt % to about 82.5 wt %, from about 60.0 wt % to about 80.0 wt %, from about 60.0 wt % to about 77.5 wt %, from about 60.0 wt % to about 75.0 wt %, from about 60.0 wt % to about 72.5 wt %, from about 60.0 wt % to about 70.0 wt %, from about 60.0 wt % to about 67.5 wt %, or from about 60.0 wt % to about 65.0 wt %.

Also included within the scope of the present disclosure are individual amounts of calcium chloride from about 6.0 wt % to about 40.0 wt %, e.g., from about 6.0 wt % to about 35.0 wt %, from about 6.0 wt % to about 30.0 wt %, from about 6.0 wt % to about 25.0 wt %, from about 6.0 wt % to about 22.5 wt %, from about 6.0 wt % to about 20.0 wt %, from about 6.0 wt % to about 17.5 wt %, from about 6.0 wt % to about 15 wt %, from about 8.0 wt % to about 40.0 wt %, from about 8.0 wt % to about 35.0 wt %, from about 8.0 wt % to about 30.0 wt %, from about 8.0 wt % to about 25.0 wt %, from about 8.0 wt % to about 22.5 wt %, from about 8.0 wt % to about 20.0 wt %, from about 8.0 wt % to about 17.5 wt %, from about 8.0 wt % to about 15 wt %, from about 10.0 wt % to about 40.0 wt %, from about 10.0 wt % to about 35.0 wt %, from about 10.0 wt % to about 30.0 wt %, from about 10.0 wt % to about 25.0 wt %, from about 10.0 wt % to about 22.5 wt %, from about 10.0 wt % to about 20.0 wt %, from about 10.0 wt % to about 17.5 wt %, from about 10.0 wt % to about 15 wt %, from about 12.5 wt % to about 40.0 wt %, from about 12.5 wt % to about 35.0 wt %, from about 12.5 wt % to about 30.0 wt %, from about 12.5 wt % to about 25.0 wt %, from about 12.5 wt % to about 22.5 wt %, from about 12.5 wt % to about 20.0 wt %, from about 12.5 wt % to about 17.5 wt %, from about 12.5 wt % to about 15 wt %, from about 15.0 wt % to about 40.0 wt %, from about 15.0 wt % to about 35.0 wt %, from about 15.0 wt % to about 30.0 wt %, from about 15.0 wt % to about 25.0 wt %, from about 15.0 wt % to about 22.5 wt %, from about 15.0 wt % to about 20.0 wt %, from about 15.0 wt % to about 17.5 wt %, from about 17.5 wt % to about 40.0 wt %, from about 17.5 wt % to about 35.0 wt %, from about 17.5 wt % to about 30.0 wt %, from about 17.5 wt % to about 25.0 wt %, from about 17.5 wt % to about 22.5 wt %, from about 17.5 wt % to about 20.0 wt %, from about 20.0 wt % to about 40.0 wt %, from about 20.0 wt % to about 35.0 wt %, from about 20.0 wt % to about 30.0 wt %, from about 20.0 wt % to about 25.0 wt %, or from about 20.0 wt % to about 22.5 wt %.

Additional therapeutic components may be added to the rinse to reduce inflammation, and/or to act as an analgesic/anaesthetic, antimicrobial, or antifungal. For example, the oral rinse composition artificial saliva may also include a therapeutically effective amount of one or more additional components that may be added to reduce inflammation, to act as an analgesic and/or anaesthetic, to act as an antimicrobial, and/or to act as an antifungal.

Although therapeutically effective amounts may vary, depending on the therapy details, on the therapeutic agent, and/or on certain characteristics of the therapeutic recipient, a therapeutically effective amount may include at least about 0.1% by weight of the therapeutic agent in the oral care mixture (e.g., at least about 0.2 wt %, at least 0.3 wt %, at least 0.4 wt %, at least 0.5 wt %, at least 0.75 wt %, at least 1.0 wt %, at least 1.5 wt %, at least 2.0 wt %, at least 2.5 wt %, at least 3.0 wt %, at least 3.5 wt %, at least 4.0 wt %, at least 4.5 wt %, at least about 5.0 wt %, at least 6.0 wt %, at least 7.0 wt %, at least 8.0 wt %, at least 9.0 wt %, at least 10.0 wt %, at least 12.0 wt %, at least 14.0 wt %, at least 16.0 wt %, at least 18.0 wt %, at least 20.0 wt %, at least 23.0 wt %, at least 26.0 wt %, at least 29.0 wt %, at least 32.0 wt %, at least 35.0 wt %, at least 38.0 wt %, at least 41.0 wt %, at least 44.0 wt %, or at least 47.0 wt %) and optionally also up to about 65.0% by weight of the therapeutic agent in the oral care mixture (e.g., up to about 60.0 wt %, up to about 55.0 wt %, up to about 52.5 wt %, up to about 50.0 wt %, up to about 47.5 wt %, up to about 45.0 wt %, up to about 42.5 wt %, up to about 40.0 wt %, up to about 37.5 wt %, up to about 35.0 wt %, up to about 32.5 wt %, up to about 30.0 wt %, up to about 25.0 wt %, up to about 20.0 wt %, up to about 15.0 wt %, up to about 10.0 wt %, or up to about 5.0 wt %). Additionally or alternatively, in embodiments in which the oral rinse composition (and/or artificial saliva comprising, consisting essentially of, or consisting of the oral rinse composition) includes water in addition to the oral care mixture, the therapeutically effective amount may be expressed as a w/v % in aqueous solution, and may include at least about 0.01 w/v % of the therapeutic agent in the oral rinse composition (and/or in the artificial saliva), e.g., at least about 0.05 w/v %, at least about 0.1 w/v %, at least about 0.2 w/v %, at least 0.3 w/v %, at least 0.4 w/v %, at least 0.5 w/v %, at least 0.75 w/v %, at least 1.0 w/v %, at least 1.5 w/v %, at least 2.0 w/v %, at least 2.5 w/v %, at least 3.0 w/v %, at least 3.5 w/v %, at least 4.0 w/v %, at least 4.5 w/v %, at least about 5.0 w/v %, at least 6.0 w/v %, at least 7.0 w/v %, at least 8.0 w/v %, at least 9.0 w/v %, at least 10.0 w/v %, at least 12.0 w/v %, at least 14.0 w/v %, at least 16.0 w/v %, at least 18.0 w/v %, at least 20.0 w/v %, at least 23.0 w/v %, at least 26.0 w/v %, at least 29.0 w/v %, at least 32.0 w/v %, or at least 35.0 w/v %) and optionally also up to about 50 w/v % of the therapeutic agent in the oral rinse composition (and/or in the artificial saliva), e.g., up to about 47.5 w/v %, up to about 45.0 w/v %, up to about 42.5 w/v %, up to about 40.0 w/v %, up to about 37.5 w/v %, up to about 35.0 w/v %, up to about 32.5 w/v %, up to about 30.0 w/v %, up to about 25.0 w/v %, up to about 20.0 w/v %, up to about 15.0 w/v %, up to about 10.0 w/v %, up to about 5.0 w/v %, up to about 3.0 w/v %, or up to about 1.0 w/v %. In particular embodiments, the therapeutic agent may be present in the oral care mixture in an amount such that, when about 0.1 oz (about 3 mL) of water is added to the oral care mixture, the oral rinse composition (and/or the artificial saliva) may exhibit at least about 0.1 w/v %, at least about 0.5 w/v %, at least about 1.0 w/v %, or at least about 5.0 w/v % of the therapeutic agent.

For example, a therapeutically effective amount of benzocaine and/or lidocaine, when present as an analgesic and/or anaesthetic, may include, based on the weight of the oral care mixture, from about 1.0 wt % to about 60.0 wt %, from about 1.0 wt % to about 55.0 wt %, from about 1.0 wt % to about 52.5 wt %, from about 1.0 wt % to about 50.0 wt %, from about 1.0 wt % to about 47.5 wt %, from about 1.0 wt % to about 45.0 wt %, from about 1.0 wt % to about 42.5 wt %, from about 1.0 wt % to about 40.0 wt %, from about 1.0 wt % to about 37.5 wt %, from about 1.0 wt % to about 35.0 wt %, from about 1.0 wt % to about 32.5 wt %, from about 1.0 wt % to about 30.0 wt %, from about 2.0 wt % to about 60.0 wt %, from about 2.0 wt % to about 55.0 wt %, from about 2.0 wt % to about 52.5 wt %, from about 2.0 wt % to about 50.0 wt %, from about 2.0 wt % to about 47.5 wt %, from about 2.0 wt % to about 45.0 wt %, from about 2.0 wt % to about 42.5 wt %, from about 2.0 wt % to about 40.0 wt %, from about 2.0 wt % to about 37.5 wt %, from about 2.0 wt % to about 35.0 wt %, from about 2.0 wt % to about 32.5 wt %, from about 2.0 wt % to about 30.0 wt %, from about 3.0 wt % to about 60.0 wt %, from about 3.0 wt % to about 55.0 wt %, from about 3.0 wt % to about 52.5 wt %, from about 3.0 wt % to about 50.0 wt %, from about 3.0 wt % to about 47.5 wt %, from about 3.0 wt % to about 45.0 wt %, from about 3.0 wt % to about 42.5 wt %, from about 3.0 wt % to about 40.0 wt %, from about 3.0 wt % to about 37.5 wt %, from about 3.0 wt % to about 35.0 wt %, from about 3.0 wt % to about 32.5 wt %, from about 3.0 wt % to about 30.0 wt %, from about 5.0 wt % to about 60.0 wt %, from about 5.0 wt % to about 55.0 wt %, from about 5.0 wt % to about 52.5 wt %, from about 5.0 wt % to about 50.0 wt %, from about 5.0 wt % to about 47.5 wt %, from about 5.0 wt % to about 45.0 wt %, from about 5.0 wt % to about 42.5 wt %, from about 5.0 wt % to about 40.0 wt %, from about 5.0 wt % to about 37.5 wt %, from about 5.0 wt % to about 35.0 wt %, from about 5.0 wt % to about 32.5 wt %, from about 5.0 wt % to about 30.0 wt %, from about 7.0 wt % to about 60.0 wt %, from about 7.0 wt % to about 55.0 wt %, from about 7.0 wt % to about 52.5 wt %, from about 7.0 wt % to about 50.0 wt %, from about 7.0 wt % to about 47.5 wt %, from about 7.0 wt % to about 45.0 wt %, from about 7.0 wt % to about 42.5 wt %, from about 7.0 wt % to about 40.0 wt %, from about 7.0 wt % to about 37.5 wt %, from about 7.0 wt % to about 35.0 wt %, from about 7.0 wt % to about 32.5 wt %, from about 7.0 wt % to about 30.0 wt %, from about 10.0 wt % to about 60.0 wt %, from about 10.0 wt % to about 55.0 wt %, from about 10.0 wt % to about 52.5 wt %, from about 10.0 wt % to about 50.0 wt %, from about 10.0 wt % to about 47.5 wt %, from about 10.0 wt % to about 45.0 wt %, from about 10.0 wt % to about 42.5 wt %, from about 10.0 wt % to about 40.0 wt %, from about 10.0 wt % to about 37.5 wt %, from about 10.0 wt % to about 35.0 wt %, from about 10.0 wt % to about 32.5 wt %, from about 10.0 wt % to about 30.0 wt %, from about 20.0 wt % to about 60.0 wt %, from about 20.0 wt % to about 55.0 wt %, from about 20.0 wt % to about 52.5 wt %, from about 20.0 wt % to about 50.0 wt %, from about 20.0 wt % to about 47.5 wt %, from about 20.0 wt % to about 45.0 wt %, from about 20.0 wt % to about 42.5 wt %, from about 20.0 wt % to about 40.0 wt %, from about 20.0 wt % to about 37.5 wt %, from about 20.0 wt % to about 35.0 wt %, from about 20.0 wt % to about 32.5 wt %, from about 20.0 wt % to about 30.0 wt %, from about 30.0 wt % to about 60.0 wt %, from about 30.0 wt % to about 55.0 wt %, from about 30.0 wt % to about 52.5 wt %, from about 30.0 wt % to about 50.0 wt %, from about 30.0 wt % to about 47.5 wt %, from about 30.0 wt % to about 45.0 wt %, from about 30.0 wt % to about 42.5 wt %, from about 30.0 wt % to about 40.0 wt %, from about 30.0 wt % to about 37.5 wt %, or from about 30.0 wt % to about 35.0 wt %.

Additionally or alternatively, in embodiments in which the oral rinse composition (and/or artificial saliva comprising, consisting essentially of, or consisting of the oral rinse composition) includes water in addition to the oral care mixture, the therapeutically effective amount of benzocaine and/or lidocaine may be from about 0.1 w/v % to about 50.0 w/v %, from about 0.1 w/v % to about 47.5 w/v %, from about 0.1 w/v % to about 45.0 w/v %, from about 0.1 w/v % to about 42.5 w/v %, from about 0.1 w/v % to about 40.0 w/v %, from about 0.1 w/v % to about 37.5 w/v %, from about 0.1 w/v % to about 35.0 w/v %, from about 0.1 w/v % to about 32.5 w/v %, from about 0.1 w/v % to about 30.0 w/v %, from about 0.1 w/v % to about 25.0 w/v %, from about 0.1 w/v % to about 20.0 w/v %, from about 0.1 w/v % to about 15.0 w/v %, from about 0.1 w/v % to about 10.0 w/v %, from about 0.1 w/v % to about 5.0 w/v %, from about 0.5 w/v % to about 50.0 w/v %, from about 0.5 w/v % to about 47.5 w/v %, from about 0.5 w/v % to about 45.0 w/v %, from about 0.5 w/v % to about 42.5 w/v %, from about 0.5 w/v % to about 40.0 w/v %, from about 0.5 w/v % to about 37.5 w/v %, from about 0.5 w/v % to about 35.0 w/v %, from about 0.5 w/v % to about 32.5 w/v %, from about 0.5 w/v % to about 30.0 w/v %, from about 0.5 w/v % to about 25.0 w/v %, from about 0.5 w/v % to about 20.0 w/v %, from about 0.5 w/v % to about 15.0 w/v %, from about 0.5 w/v % to about 10.0 w/v %, from about 0.5 w/v % to about 5.0 w/v %, from about 1.0 w/v % to about 50.0 w/v %, from about 1.0 w/v % to about 47.5 w/v %, from about 1.0 w/v % to about 45.0 w/v %, from about 1.0 w/v % to about 42.5 w/v %, from about 1.0 w/v % to about 40.0 w/v %, from about 1.0 w/v % to about 37.5 w/v %, from about 1.0 w/v % to about 35.0 w/v %, from about 1.0 w/v % to about 32.5 w/v %, from about 1.0 w/v % to about 30.0 w/v %, from about 1.0 w/v % to about 25.0 w/v %, from about 1.0 w/v % to about 20.0 w/v %, from about 1.0 w/v % to about 15.0 w/v %, from about 1.0 w/v % to about 10.0 w/v %, from about 1.0 w/v % to about 5.0 w/v %, from about 2.0 w/v % to about 50.0 w/v %, from about 2.0 w/v % to about 47.5 w/v %, from about 2.0 w/v % to about 45.0 w/v %, from about 2.0 w/v % to about 42.5 w/v %, from about 2.0 w/v % to about 40.0 w/v %, from about 2.0 w/v % to about 37.5 w/v %, from about 2.0 w/v % to about 35.0 w/v %, from about 2.0 w/v % to about 32.5 w/v %, from about 2.0 w/v % to about 30.0 w/v %, from about 2.0 w/v % to about 25.0 w/v %, from about 2.0 w/v % to about 20.0 w/v %, from about 2.0 w/v % to about 15.0 w/v %, from about 2.0 w/v % to about 10.0 w/v %, from about 2.0 w/v % to about 5.0 w/v %, from about 3.0 w/v % to about 50.0 w/v %, from about 3.0 w/v % to about 47.5 w/v %, from about 3.0 w/v % to about 45.0 w/v %, from about 3.0 w/v % to about 42.5 w/v %, from about 3.0 w/v % to about 40.0 w/v %, from about 3.0 w/v % to about 37.5 w/v %, from about 3.0 w/v % to about 35.0 w/v %, from about 3.0 w/v % to about 32.5 w/v %, from about 3.0 w/v % to about 30.0 w/v %, from about 3.0 w/v % to about 25.0 w/v %, from about 3.0 w/v % to about 20.0 w/v %, from about 3.0 w/v % to about 15.0 w/v %, from about 3.0 w/v % to about 10.0 w/v %, from about 3.0 w/v % to about 5.0 w/v %, from about 5.0 w/v % to about 50.0 w/v %, from about 5.0 w/v % to about 47.5 w/v %, from about 5.0 w/v % to about 45.0 w/v %, from about 5.0 w/v % to about 42.5 w/v %, from about 5.0 w/v % to about 40.0 w/v %, from about 5.0 w/v % to about 37.5 w/v %, from about 5.0 w/v % to about 35.0 w/v %, from about 5.0 w/v % to about 32.5 w/v %, from about 5.0 w/v % to about 30.0 w/v %, from about 5.0 w/v % to about 25.0 w/v %, from about 5.0 w/v % to about 20.0 w/v %, from about 5.0 w/v % to about 15.0 w/v %, from about 5.0 w/v % to about 10.0 w/v %, from about 7.0 w/v % to about 50.0 w/v %, from about 7.0 w/v % to about 47.5 w/v %, from about 7.0 w/v % to about 45.0 w/v %, from about 7.0 w/v % to about 42.5 w/v %, from about 7.0 w/v % to about 40.0 w/v %, from about 7.0 w/v % to about 37.5 w/v %, from about 7.0 w/v % to about 35.0 w/v %, from about 7.0 w/v % to about 32.5 w/v %, from about 7.0 w/v % to about 30.0 w/v %, from about 7.0 w/v % to about 25.0 w/v %, from about 7.0 w/v % to about 20.0 w/v %, from about 7.0 w/v % to about 15.0 w/v %, from about 7.0 w/v % to about 10.0 w/v %, from about 10.0 w/v % to about 50.0 w/v %, from about 10.0 w/v % to about 47.5 w/v %, from about 10.0 w/v % to about 45.0 w/v %, from about 10.0 w/v % to about 42.5 w/v %, from about 10.0 w/v % to about 40.0 w/v %, from about 10.0 w/v % to about 37.5 w/v %, from about 10.0 w/v % to about 35.0 w/v %, from about 10.0 w/v % to about 32.5 w/v %, from about 10.0 w/v % to about 30.0 w/v %, from about 10.0 w/v % to about 25.0 w/v %, from about 10.0 w/v % to about 20.0 w/v %, or from about 10.0 w/v % to about 15.0 w/v %.

In view of the entirety of the present disclosure, including the claims, a person having ordinary skill in the art will readily recognize that the present disclosure introduces a composition comprising an oral care mixture for use in a human oral cavity, the oral care mixture comprising: monobasic sodium phosphate; dibasic sodium phosphate; sodium bicarbonate; sodium chloride; and calcium chloride.

The oral care mixture may comprise, by weight: between about 0.5% and about 5.0% of monobasic sodium phosphate; between about 0.5% and about 5.0% dibasic sodium phosphate; between about 1.0% and about 10.0% of sodium bicarbonate; between about 55.0% and about 87.5% of sodium chloride; and between about 10.0% and about 30.0% of calcium chloride.

The oral care mixture may comprise, by weight: about 2.8% monobasic sodium phosphate; about 2.8% dibasic sodium phosphate; about 4.6% sodium bicarbonate; about 72.6% sodium chloride; and about 14.2% calcium chloride.

The oral care mixture may further comprise silicon dioxide. For example, the oral care mixture may comprise, by weight: between about 0.5% and about 5.0% of monobasic sodium phosphate; between about 0.5% and about 5.0% dibasic sodium phosphate; between about 1.0% and about 10.0% of sodium bicarbonate; between about 55.0% and about 87.5% of sodium chloride; between about 10.0% and about 30.0% of calcium chloride; and between about 0.5% and about 5.0% silicon dioxide. In another example, the oral care mixture may comprise, by weight: about 2.7% monobasic sodium phosphate; about 2.7% dibasic sodium phosphate; about 4.3% sodium bicarbonate; about 68.9% sodium chloride; about 18.6% calcium chloride; and about 2.7% silicon dioxide.

The oral care mixture may further comprise at least one of an anti-inflammatory, an analgesic and/or anesthetic, an antimicrobial, and an antifungal. The anti-inflammatory may be or comprise one or more of diclofenac, felbinac, ketoprofen, and piroxicam. The analgesic and/or anesthetic may be or comprise one or more of capsaicin, eugenol, guaiacol, lidocaine, benzocaine, acemannan, oil of cinnamon, and oil of clove. The antimicrobial may be or comprise one or more of xylitol, calcium alginate, chitosan, iodoform, and chlorobutanol. The antifungal may be or comprise one or more of chlorobutanol, nystatin, clotrimazole, and amphotericin B.

The oral care mixture may be for dissolving in water to form an oral rinse solution.

The composition may further comprise water, and the composition may be an oral rinse solution.

The composition may relieve symptoms of dryness of the oral cavity.

The present disclosure also introduces a composition consisting of an oral care mixture for use in a human oral cavity, the oral care mixture consisting of: monobasic sodium phosphate; dibasic sodium phosphate; sodium bicarbonate; sodium chloride; and calcium chloride.

The oral care mixture may consist of, by weight: between about 0.5% and about 5.0% of monobasic sodium phosphate; between about 0.5% and about 5.0% dibasic sodium phosphate; between about 1.0% and about 10.0% of sodium bicarbonate; between about 55.0% and about 87.5% of sodium chloride; and between about 10.0% and about 30.0% of calcium chloride.

The oral care mixture may consist of, by weight: about 2.8% monobasic sodium phosphate; about 2.8% dibasic sodium phosphate; about 4.6% sodium bicarbonate; about 72.6% sodium chloride; and about 14.2% calcium chloride.

The present disclosure also introduces a composition comprising an oral care mixture for use in a human oral cavity, the oral care mixture comprising: monobasic sodium phosphate; dibasic sodium phosphate; sodium chloride; and calcium chloride.

The oral care mixture may further comprise silicon dioxide.

The oral care mixture may further comprise at least one of an anti-inflammatory, an analgesic and/or anesthetic, an antimicrobial, and an antifungal. The anti-inflammatory may be or comprise one or more of diclofenac, felbinac, ketoprofen, and piroxicam. The analgesic and/or anesthetic may be or comprise one or more of capsaicin, eugenol, guaiacol, lidocaine, benzocaine, acemannan, oil of cinnamon, and oil of clove. The antimicrobial may be or comprise one or more of xylitol, calcium alginate, chitosan, iodoform, and chlorobutanol. The antifungal may be or comprise one or more of chlorobutanol, nystatin, clotrimazole, and amphotericin B.

The oral care mixture may be for dissolving in water to form an oral rinse solution.

The composition may further comprise water, and the composition may be an oral rinse solution.

The present disclosure also introduces an oral rinse composition comprising, consisting essentially of, or consisting of an oral care mixture to be dissolved in water to form an oral rinse solution for use in a human oral cavity, e.g., to relieve symptoms of dryness of the oral cavity. The oral care mixture may consist essentially of, by weight: from 0.5% to 5.0% of monobasic sodium phosphate; from 0.5% to 5.0% dibasic sodium phosphate; optionally from 1.0% to 10.0% of sodium bicarbonate; from 40.0% to 75.0% of sodium chloride; from 10.0% to 30.0% of calcium chloride; optionally from 0.5% to 5.0% of silicon dioxide; a therapeutically effective amount of an analgesic and/or anaesthetic selected from the group consisting of benzocaine, lidocaine, and a combination thereof; optionally a therapeutically effective amount of an anti-inflammatory selected from the group consisting of diclofenac, felbinac, ketoprofen, piroxicam, and combinations thereof; optionally a therapeutically effective amount of an antimicrobial selected from the group consisting of xylitol, calcium alginate, chitosan, iodoform, chlorobutanol, and combinations thereof; optionally a therapeutically effective amount of an antifungal selected from the group consisting of chlorobutanol, nystatin, clotrimazole, amphotericin B, and combinations thereof; and optionally a therapeutically effective amount of an additional analgesic and/or anaesthetic selected from the group consisting of capsaicin, eugenol, guaiacol, acemannan, oil of cinnamon, oil of clove, and combinations thereof.

The oral care mixture may alternatively consist essentially of, by weight: from 0.5% to 5.0% of monobasic sodium phosphate; from 0.5% to 5.0% dibasic sodium phosphate; from 40.0% to 75.0% of sodium chloride; from 10.0% to 30.0% of calcium chloride; optionally from 0.5% to 5.0% of silicon dioxide; and a therapeutically effective amount of an analgesic and/or anaesthetic selected from the group consisting of benzocaine, lidocaine, and a combination thereof. The oral care mixture may alternatively consist of, by weight: from 0.5% to 5.0% of monobasic sodium phosphate; from 0.5% to 5.0% dibasic sodium phosphate; from 40.0% to 75.0% of sodium chloride; from 10.0% to 30.0% of calcium chloride; optionally from 0.5% to 5.0% of silicon dioxide; a therapeutically effective amount of benzocaine as an analgesic and/or anaesthetic.

The oral rinse composition may comprise, consist essentially of, or consist of water, an optional pH adjusting agent, and the oral care mixture, so as to form a supersaturated calcium phosphate solution. In such embodiments, the oral rinse composition may exhibit an in-solution pH in a range of from 6.25 to 7.5 (e.g., of about 6.69). In some embodiments, no additional pH adjusting agent is present in the oral rinse composition.

Artificial saliva, according to the present disclosure, may comprise, consist essentially of, or consist of the oral rinse compositions described in the present disclosure.

In any of these embodiments, the therapeutically effective amount of benzocaine and/or lidocaine may be from about 5.0% to about 50.0% by weight of the oral care mixture and/or, when the oral rinse composition (and/or artificial saliva comprising, consisting essentially of, or consisting of the oral rinse composition) includes water, the therapeutically effective amount of benzocaine and/or lidocaine as analgesic and/or anaesthetic may be such that the oral rinse composition (and/or the artificial saliva) contains at least a 5.0 w/v % solution of benzocaine and/or lidocaine in about 0.1 oz (about 3 mL) of water.

The foregoing outlines features of several embodiments so that a person having ordinary skill in the art may better understand the aspects of the present disclosure. A person having ordinary skill in the art should appreciate that they may readily use the present disclosure as a basis for designing or modifying other processes and structures for carrying out the same functions and/or achieving the same benefits of the embodiments introduced herein. A person having ordinary skill in the art should also realize that such equivalent constructions do not depart from the spirit and scope of the present disclosure, and that they may make various changes, substitutions and alterations herein without departing from the spirit and scope of the present disclosure.

The Abstract at the end of this disclosure is provided to comply with 37 C.F.R. .sctn.1.72(b) to permit the reader to quickly ascertain the nature of the technical disclosure. It is submitted with the understanding that it will not be used to interpret or limit the scope or meaning of the claims.

What is claimed is:

1. An oral rinse composition comprising an oral care mixture to be dissolved in water to form an oral rinse solution, supersaturated in calcium phosphate, for use in a human oral cavity, wherein the oral care mixture consists of, by weight:
   from 0.5% to 5.0% of monobasic sodium phosphate;
   from 0.5% to 5.0% dibasic sodium phosphate;
   from 40.0% to 75.0% of sodium chloride;
   from 10.0% to 30.0% of calcium chloride;
   from 0.5% to 5.0% of silicon dioxide; and
   a therapeutically effective amount of benzocaine and/or lidocaine as an analgesic and/or anaesthetic.

2. The oral rinse composition of claim 1 wherein the therapeutically effective amount of benzocaine and/or lidocaine is from 5.0% to 50.0%, by weight.

3. The oral rinse composition of claim 1 wherein the therapeutically effective amount of benzocaine and/or lidocaine is such that the composition provides at least a 5.0 w/v % solution of benzocaine and/or lidocaine when the composition is dissolved in 0.1 oz (3 mL) of water.

4. An oral rinse solution consisting of water and the oral care mixture of claim 1 dissolved therein to form a supersaturated calcium phosphate solution.

5. Artificial saliva consisting essentially of the oral rinse solution of claim 4.

6. An oral rinse solution consisting of water and the oral care mixture of claim 2 dissolved therein to form a supersaturated calcium phosphate solution.

7. Artificial saliva consisting essentially of the oral rinse solution of claim 6.

8. An oral rinse solution consisting of water and the oral care mixture of claim 3 dissolved therein to form a supersaturated calcium phosphate solution.

9. Artificial saliva consisting essentially of the oral rinse solution of claim 8.

* * * * *